United States Patent [19]

Tomasulo

[11] Patent Number: 4,542,345

[45] Date of Patent: Sep. 17, 1985

[54] MULTI-ELEMENT THERMOELECTRIC NON-DESTRUCTIVE TESTING DEVICE AND METHOD

[75] Inventor: Walter Tomasulo, Wayne, N.J.

[73] Assignee: Technicorp, East Rutherford, N.J.

[21] Appl. No.: 492,698

[22] Filed: May 9, 1983

[51] Int. Cl.$^4$ ............................................. G01N 25/00
[52] U.S. Cl. ....................................... 324/451; 374/45
[58] Field of Search ............... 324/451, 73 R, 73 PC, 324/158 P, 158 F; 374/45

[56] References Cited

U.S. PATENT DOCUMENTS 3,011,120 11/1961 Brown et al. .......................... 374/45
4,342,957 8/1982 Russell .............................. 324/73 R

FOREIGN PATENT DOCUMENTS 530235 5/1977 U.S.S.R. .............................. 324/451
529401 6/1977 U.S.S.R. .............................. 324/451

Primary Examiner—Ernest F. Karlsen
Assistant Examiner—Kevin D. O'Shea
Attorney, Agent, or Firm—Samuelson & Jacob

[57] ABSTRACT

A non-destructive testing device and method in which information is obtained from a plurality of thermoelectric junctions made between an unknown material and a plurality of test elements of different known characteristics to provide data for identifying the unknown material.

19 Claims, 6 Drawing Figures

MULTI-ELEMENT THERMOELECTRIC NON-DESTRUCTIVE TESTING DEVICE AND METHOD

The present invention relates generally to the identification of unknown materials and pertains, more specifically, to non-destructive testing devices and methods used for identifying given unknown materials utilizing information obtained from thermoelectric junctions established between the testing devices and the unknown materials.

Thermoelectric instruments and methods for testing materials have been in use for some time now in identifying unknown materials by making use of the well-known thermocouple principle to obtain data which enables identification of a particular unknown material. Basically, these instruments and methods form a junction between a known material and the unknown material, heat the junction, and measure the voltage generated at the junction. Since the voltage is a function of the materials and the temperature at the junction and will differ from material to material, the thermoelectric voltage may be used to identify the particular unknown material in the junction. Unfortunately, however, the differences in the thermoelectric voltage from one unknown material to another, when placed in a heated junction with any one particular known material, very often are not of sufficient magnitude to enable easy discrimination, and hence accurate identification, of one unknown material over another. This is true particularly among the wide variety of currently available alloys, many of which tend to exhibit very similar thermoelectric voltages with any one selected known material.

It is an object of the present invention to provide a thermoelectric testing device and method which will identify unknown materials more positively and with greater accuracy than previous devices and methods.

Another object of the invention is to provide a thermoelectric testing device and method which will identify a wider variety of unknown materials with accuracy.

Still another object of the invention is to provide a thermoelectric testing device and method which will identify more accurately different unknown materials having very similar thermoelectric properties when placed in a thermoelectric junction with a particular known material.

Yet another object of the invention is to provide a thermoelectric testing device and method which are easy to use in attaining more accurate and positive results in the identification of a variety of unknown materials.

The above objects, as well as still further objects and advantages, are attained by the present invention which may be described briefly as a non-destructive testing device and method for identifying a given unknown material utilizing information obtained from a plurality of thermoelectric junctions established between the testing device and the unknown material, the testing device and method providing a plurality of thermoelectric junction-forming test elements, each test element having a known characteristic selected to be different from the corresponding selected known characteristics of the other test elements such that thermoelectric junctions established between the test elements and the given unknown material will produce different thermoelectric information for each junction, test means for and the step of presenting each test element to the given unknown material and establishing the thermoelectric junctions, and information means for and the step of receiving the thermoelectric information from each thermoelectric junction and providing identifying data pertaining to the given unknown material based upon the thermoelectric information received from the thermoelectric junctions.

The invention will be more fully understood, while still further objects and advantages will become apparent, in the following detailed description of a preferred embodiment of the invention illustrated in the accompanying drawing, in which.

Figure 1:
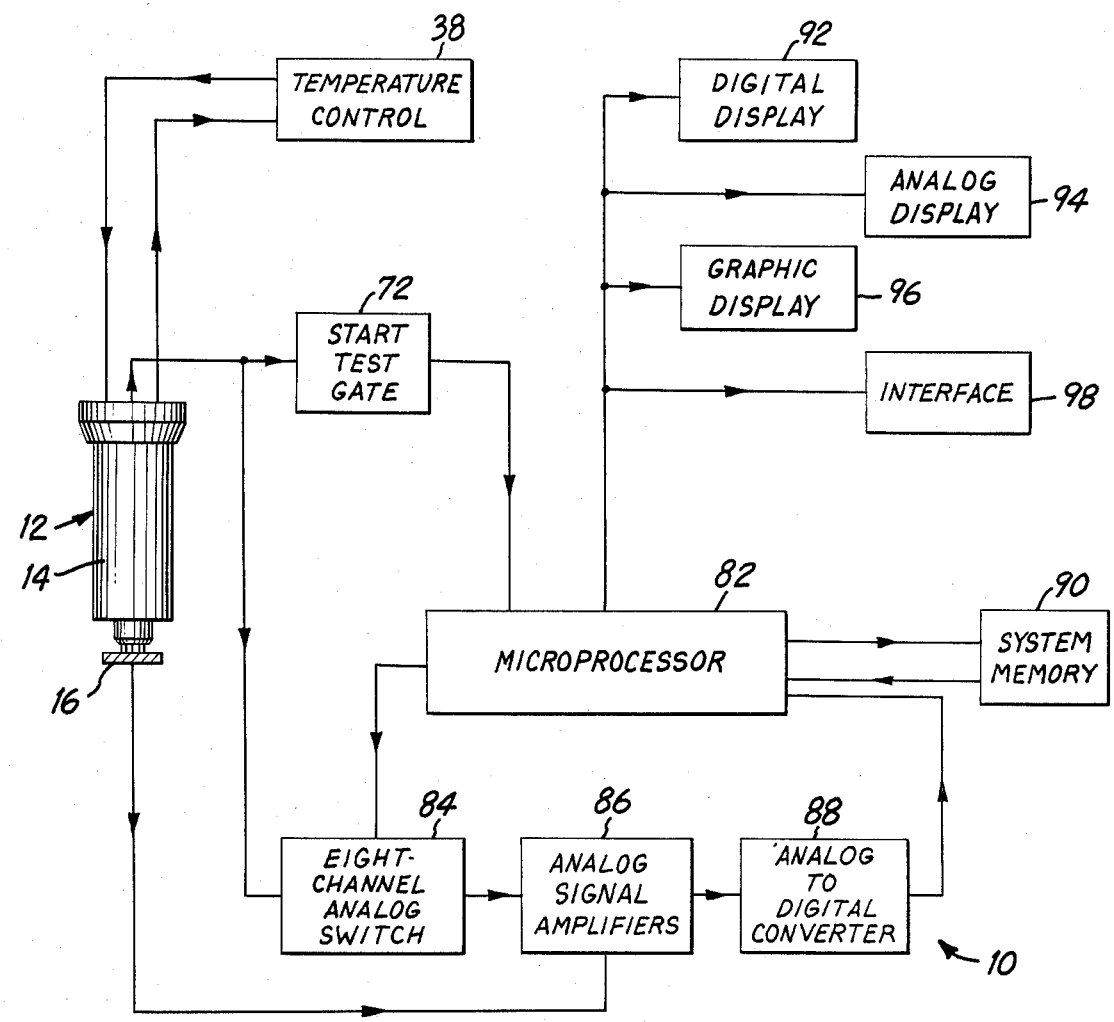
FIG. 1 is a block diagram illustrating a system in which the device and method of the invention is operated.

Referring now to the drawing, and especially to FIG. 1 thereof, a block diagram 10 illustrates a system in which a testing device 12 operates, all in accordance with the present invention. Block diagram 10 illustrates diagrammatically the manner in which a probe assembly 14 is associated with a test specimen 16 of unknown material to obtain thermoelectric information which then is processed to provide data for the identification of the unknown material of test specimen 16.

Figure 2:
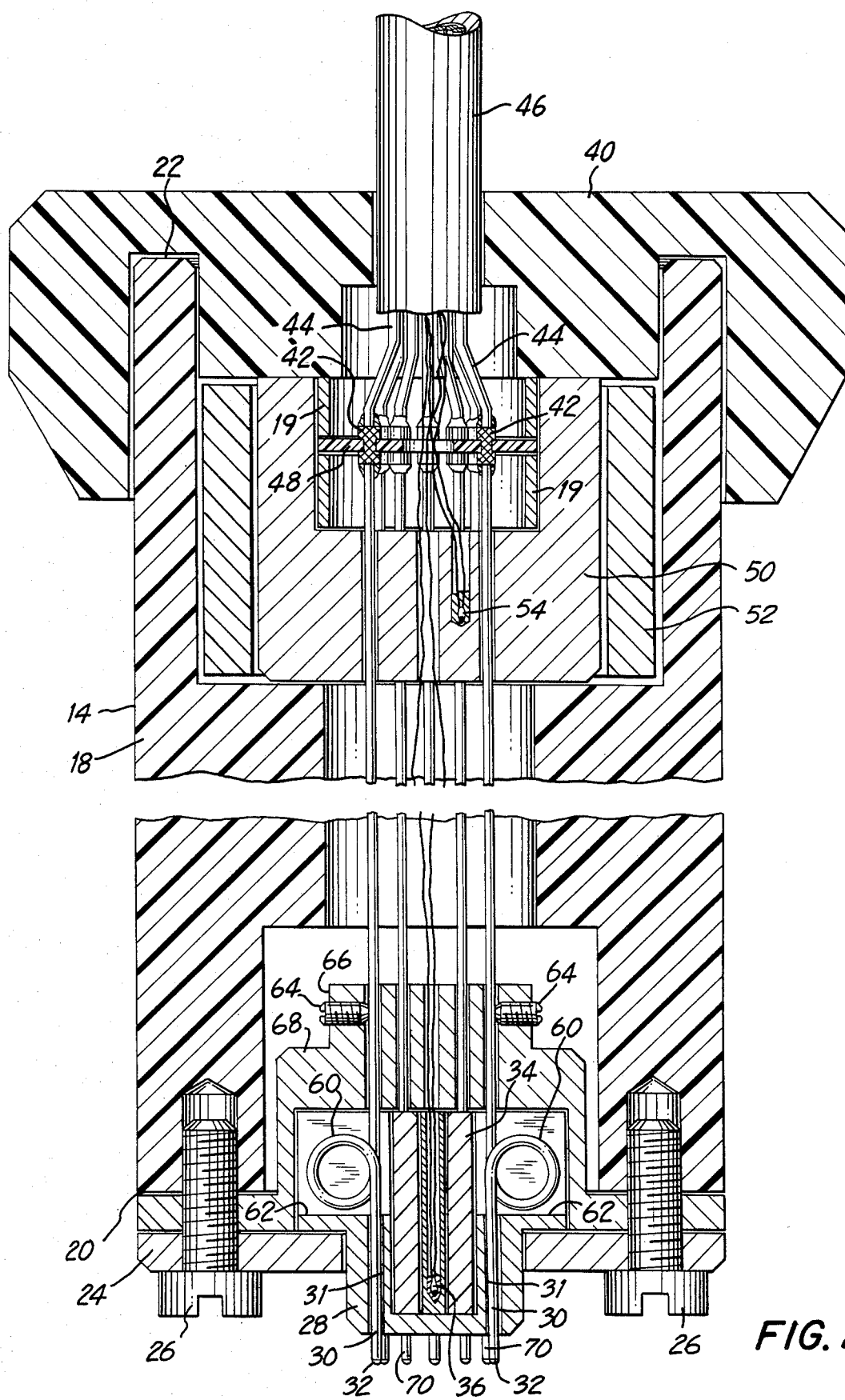
FIG. 2 is a longitudinal cross-sectional view of the probe assembly of the device, taken along line 2—2 of FIG. 3.
Figure 3:
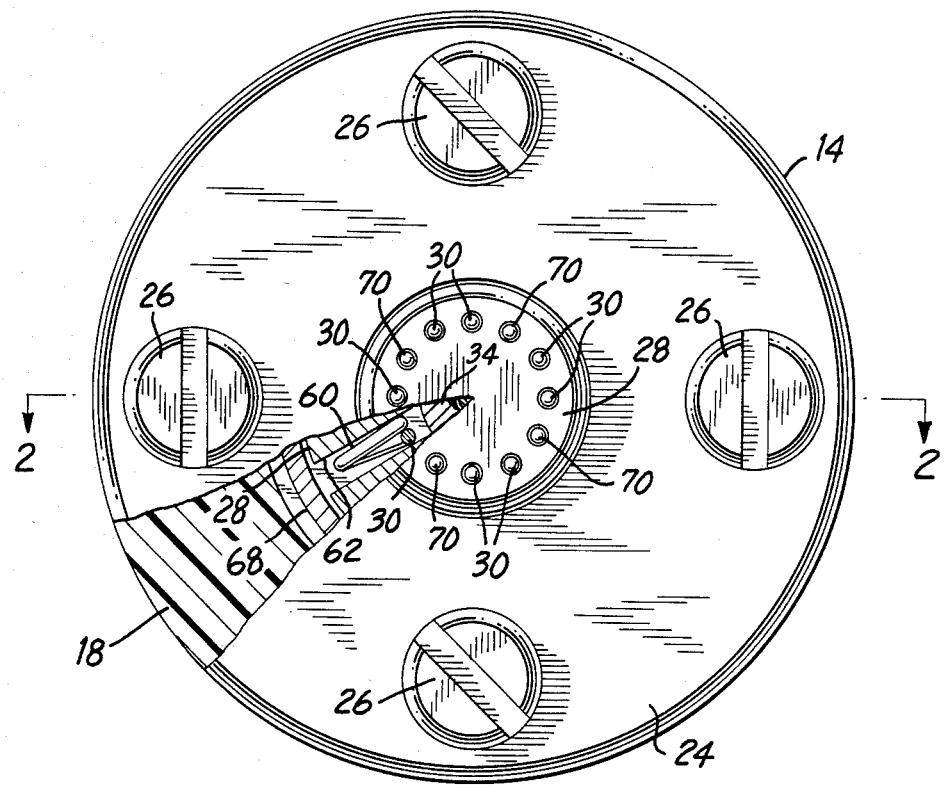
FIG. 3 is a partially cut-away bottom plan view of the probe assembly of FIG. 2.

Turning now to FIGS. 2 and 3, as well as to FIG. 1, probe assembly 14 is seen to include an elongate probe housing 18 having a contact end 20 and an opposite remote end 22. A retainer ring 24 is secured to the contact end 20 by threaded fasteners 26 and holds a contact block 28 in place at the contact end 20 of the probe housing 18. A plurality of test elements shown in the form of test rods 30 extend through corresponding guide holes 31 in contact block 28, each test rod 30 including a terminal end 32 which serves to contact the test specimen 16. An electrically powered heater 34 heats contact block 28 which, in turn, heats the test rods 30 to provide the elevated temperature required at the junction between the terminal end 32 of each test rod 30 and the test specimen 16. A temperature sensing element in the form of a thermistor 36 is placed within contact block 28 and is coupled to a temperature control 38 (see FIG. 1) for controlling the temperature of the contact block 28 and of the test rods 30.

At the remote end 22 of probe housing 18, a cap 40 encloses the junctions 42 made between the test rods 30 and the conductors 44 of a control cable 46 which connects the probe assembly 14 with the remainder of the system. Junctions 42 are supported in a terminal board 48 mounted by means of sleeves 19 of insulating material within an upper block 50 which is heated by an electrically powered heater 52 to raise the temperature of junctions 42 above ambient temperature. A second temperature sensing element in the form of a second thermistor 54 is placed within the upper block 50 and is coupled to temperature control 38 for controlling the temperature of upper block 50 and the junctions 42. By setting the temperature of junctions 42 at some level above ambient temperature, but far below the temperature set at the contact block 28 and the terminal ends 32 of test rods 30, the thermoelectric voltages generated at junctions 42 remain stable and known so that accuracy is assured in any measurement of thermoelectric voltages at the terminal ends 32 of test rods 30.

The test rods 30 themselves are coated with a very thin coating of dielectric material, such as a thin coating of Teflon, in order to isolate the test rods 30 from the contact block 28 and the upper block 50, as well as from one another. The coating is thin enough to enable appropriate heating of the test rods 30.

In order to assure repeatable accuracy among the thermoelectric voltages measured at each thermoelectric junction between a terminal end 32 of a test rod 30 and the test specimen 16, the pressures with which the test rods 30 are urged into contact with the test specimen 16 are essentially equalized by means of a torsion spring provided by a loop 60 placed in each test rod 30. Each loop 60 biases a corresponding test rod 30 longitudinally toward the test specimen 30 and is confined against lateral movement by being contained within a corresponding individual guide chamber 62 and each test rod 30 is anchored, as by the use of a set screw 64 threaded through a collar portion 66 of an anchor block 68 secured to the probe housing 18. The dimensions of each loop 60 are selected so that the pressures at the terminal ends 32 of the test rods 30 are equalized when the probe assembly 14 is urged against test specimen 16.

As best seen in FIG. 3, the preferred arrangement of the test rods 30 places the test rods in a circular array, with each test rod located on the circumference of a circle. In the illustrated embodiment there are shown eight test rods 30 to by used for obtaining thermoelectric information from eight corresponding thermoelectric junctions; however, a number other than eight may be employed. In order to assure that the terminal ends 32 of all eight of the test rods 30 are placed in appropriate contact with test specimen 16, probe assembly 14 includes a plurality of contact-sensing elements shown in the form of contact rods 70 each having essentially the same configuration as the test rods 30. Contact rods 70 are interspersed within the circular array of test rods 30 so that when contact is made between all of the contact rods 70 and the test specimen 16, each of the test rods 30 also will be in contact with the test specimen 16. Thus, contact rods 70 do not participate in producing thermoelectric information, but are so located within the array of test rods 30 as to assure that all of the test rods are in appropriate contact with the test specimen 16 before thermoelectric voltage are measured. To this end, contact rods 70 are placed ninety degrees apart in the circular array of test rods 30 and contact rods 70.

Figure 4:
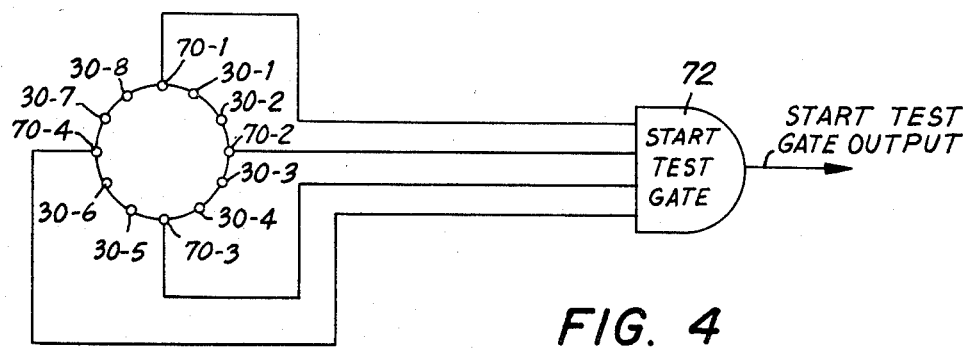
FIG. 4 is a schematic diagram of a portion of the probe coupled to the system of FIG. 1.

The operation of contact rods 70 in connection with the circular array is shown schematically in FIG. 4. The eight test rods are seen at 30-1, 30-2, 30-3, 30-4, 30-5, 30-6 30-7 and 30-8. The four contact rods are shown at 70-1, 70-2, 70-3 and 70-4. The contact rods 70 are fabricated of a material which is not necessarily thermoelectrically active, but which will produce an output when in contact with the test specimen 16. A suitable material is brass, although other materials are available which will perform the same function. When the contact end 20 of probe assembly 14 is placed against the test specimen 16, the output from each contact rod 70 is directed to a start test gate 72. Start test gate 72 is an AND gate and will provide a start test signal at the output thereof only when an input is received essentially simultaneously from all four of the contact rods 70. Since it would be highly unlikely that all four contact rods 70 will produce an output simultaneously without all eight of the test rods 30 being in contact with the test specimen 16, the aforesaid arrangement assures that thermoelectric information is not obtained until all of the thermoelectric junctions are made properly, with essentially equalized pressure, for accuracy of measurement.

As described above, in connection with FIGS. 1 and 2, the contact block 28 is heated by heater 34 to heat test rods 30 so as to provide the heated junctions between terminal ends 32 and test specimen 16. At the same time, heater 52 heats upper block 50 to heat junctions 42. Temperature control 38 maintains the temperature of contact block 28 far higher than the temperature of upper block 50. Typically the temperature of contact block 28 is maintained at about 300° F., while the temperature of upper block 50 is held at about 100° F. Sufficient heat is transferred from contact block 28 to the test rods 30 for providing the required heated junctions by virtue of the relative dimensions of the contact block 28 and the test rods 30. Thus, by assuring that the guide holes 31 each have a length far greater than the diameter of the corresponding test rod 30 passing through the guide hole, sufficient heat is transferred to the test rods. By way of example, the diameter of each test rod may be about 0.020 to 0.030 inch, with a dielectric coating having a thickness of about 0.0005 inch, and the guide holes 31 have an inside diameter great enough to provide about 0.001 inch clearance between a coated test rod and the contact block. The length of each guide hole 31 is at least approximately ten times the diameter of a test rod 30 so that adequate heat transfer is assured. The dielectric coating on each test rod 30 does not extend over the terminal end 32 so that direct contact is made between the material of each test rod 30 and the test specimen 16.

The materials of the test rods 30 themselves may be chosen from among a very wide variety of suitable materials. A sampling of some of the materials which provide suitable results are: iron, copper, silicon carbide, silver, nickel, titanium, gold, columbium (niobium), 410 SST, Inconel 600, BeCu, 17-4Ph, 6Al-4V titanium, 90/10, 50Ni/50 Fe, 50Ni/50Cr, 302 SST and 70/30. Other materials will be apparent to those skilled in the art of materials. For illustrative purposes, the following table sets forth eight particular materials chosen for each of the eight test rods 30 and tabulates thermoelectric information in terms of thermoelectric voltage obtained at each junction between the terminal end 32 of the corresponding test rod 30 and each of two test specimens 16, the thermoelectric junctions being heated to about 300° F.:

| TEST ROD | TEST ROD MATERIAL | TEST SPECIMEN | |
|---|---|---|---|
| | | COPPER | IRON/NICKEL |
| 30-1 | 410 SST | 7.3 mv | 4.6 mv |
| 30-2 | 302 SST | 6.0 mv | 4.5 mv |
| 30-3 | 6Al-4V TITANIUM | 5.5 mv | 4.5 mv |
| 30-4 | 70/30 | 2.4 mv | 2.3 mv |
| 30-5 | 17-4Ph | 6.7 mv | 4.6 mv |
| 30-6 | INCONEL 600 | 7.1 mv | 5.1 mv |
| 30-7 | 90/10 | 4.4 mv | 2.9 mv |
| 30-8 | COPPER | 6.1 mv | 2.6 mv |

Figure 5:
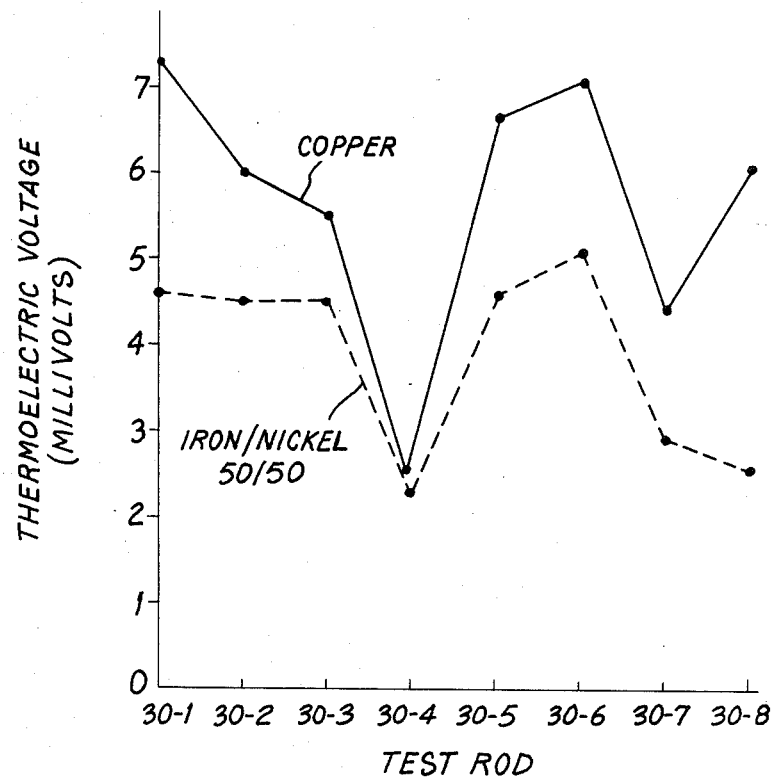
FIG. 5 is a graphical representation of typical data obtained from the device.
Figure 6:
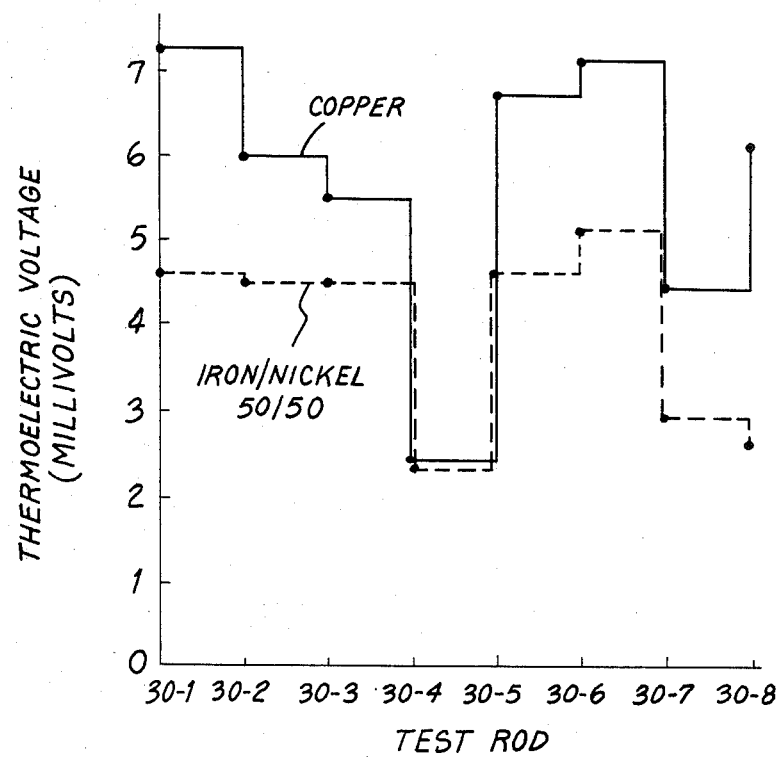
FIG. 6 is an alternate graphical representation of the data shown in FIG. 5.

The above data is plotted in FIGS. 5 and 6 wherein it becomes obvious that the composite characteristics of the total data obtained for each test specimen 16 are quite different, even though at least one point, namely, the data obtained at test rod 30-4, is so similar for both test specimens as to render accurate differentiation impractical. The plotted data illustrates that not only are the measured absolute thermoelectric voltages different for the various test rods used in conjunction with the two test specimens, but the relative directions from point to point along each plot also differ. The resulting data may be displayed in a number of ways so that the composite characteristics more positively identify a particular unknown material than any single piece of data. Thus, by utilizing data obtained essentially simultaneously from a plurality of different thermoelectric junctions, rather than from only one, an unknown material is more accurately identified with increased ease.

Returning now to FIG. 1, the thermoelectric information obtained from the probe assembly 14 is processed by testing device 12 to obtain the data which will identify a particular test specimen 16 of unknown material. Upon receiving a start test signal from start test gate 72, as explained above in connection with FIG. 4, a central processing unit in the form of a microprocessor 82 will operate to actuate an eight channel analog switch 84 to sequentially pass the thermoelectric information obtained from the eight test rods 30 to analog signal amplifiers 86 and then to an analog-to-digital converter 88 from which the digital information is supplied to the microprocessor 82. The digital information then may be stored in the system memory 90 and/or processed to provide data which will serve to identify the particular material of the test sample 16. The data may be displayed in any one of several available display devices, examples being a digital display 92 which will display identifying digital information, an analog display 94, such as a meter, or a graphic display 96 which can display data in forms such as those illustrated in FIGS. 5 and 6, as well as in other forms. In addition, an interface 98 is provided for connection to various automation devices. Thus, the composite charactericticts drawn from several thermoelectric junctions are employed to identify more precisely the particular unknown material, easily and with accuracy. While there may be similarities in information provided by establishing a thermoelectric junction between one known material and different unknown materials, which similarities render it difficult to distinguish one unknown material from another, information obtained from junctions made between a plurality of known materials and the unknown materials will provide a set of composite characteristics for each unknown material, which sets of composite characteristics will be different enough to distinguish one unknown material from another.

It is to be understood that the above detailed description of a preferred embodiment of the invention is provided by way of example only. Various details of design and construction may be modified without departing from the true spirit and scope of the invention as set forth in the appended claims.

The embodiments of the invention in which an exclusive property or privilege is claimed are as follows:

1. A non-destructive testing device used for identifying a given unknown material utilizing information obtained from a plurality of thermoelectric junctions established between the testing device and the unknown material, the testing device comprising:

a plurality of thermoelectric junction-forming test elements, each test element having a known characteristic selected to be different from the corresponding selected known characteristics of the other test elements such that thermoelectric junctions established between the test elements and the given unknown material will produce different thermoelectric information for each junction;

test means for presenting each test element to the given unknown material and establishing the thermoelectric information means for receiving the thermoelectric information from each thermoelectric junction and processing the thermoelectric information received from all the thermoelectric junctions to provide a set of composite characteristics for identifying the given unknown material based upon the set of composite characteristics derived from the thermoelectric information received from all of the thermoelectric junctions.

2. The invention of claim 1 wherein the selected known characteristics is material composition and each test element is constructed of a material having a composition different from the other test elements such that the thermoelectric information provided by each thermoelectric junction is in the form of a thermoelectric voltage related to the material composition of the test element of the corresponding thermoelectric junction.

3. The invention of claim 2 wherein the test means includes a test probe and the test elements are mounted in the test probe in fixed relation to one another.

4. The invention of claim 3 wherein the test elements are arranged in the test probe in an array for facilitating simultaneous contact of all of the test elements with the unknown material.

5. The invention of claim 4 wherein the array of test elements is a circle, with the test elements located along the circumference of the circle.

6. The invention of claim 4 including a plurality of contact-sensing elements mounted in the test probe and related to the array of test elements for providing contact information pertaining to the contact of all of the elements in the test probe with the unknown material.

7. The invention of claim 6 wherein the contact-sensing elements are located along the circumference of a circle related to the array of test elements.

8. The invention of claim 6 wherein the array of test elements is a circle, with the test elements located along the circumference of the circle, and the contact-sensing elements are located along the circumference of the circle and interspersed among the test elements.

9. The invention of claim 8 wherein the contact-sensing elements are four in number, with each contact-sensing element spaced ninety degrees along the circumference of the circle from the next adjacent contact-sensing element.

10. The invention of claim 3, 4, 5, 6, 7 or 8 including pressure-equalizing means associated with the test elements for substantially equalizing the pressures with which the test elements contact the unknown material at the thermoelectric junctions.

11. The invention of claim 10 wherein the pressure-equalizing means includes a spring integral with each test element for biasing each test element into contact with the unknown material.

12. The invention of claim 1, 2 or 3 wherein the testing device includes heating means for heating the junction-forming test elements to heat the thermoelectric junctions.

13. The invention of claim 12 wherein the heating means includes temperature control means for providing a relatively stable known temperature at the thermoelectric junctions.

14. The non-destructive testing methdd for identifying a given unknown material utilizing information obtained from a plurality of thermoelectric junctions established between a testing device and the unknown material, the testing method comprising the steps of:
providing a plurality of thermoelectric junction-forming test elements, each test element having a known characteristic selected to be different from the corresponding selected known characteristics of the other test elements such that thermoelectric junctions established between the test elements and the given unknown material will produce different thermoelectric information for each junction;
presenting each test element to the given unknown material to establish the thermoelectric junctions; and
receiving the thermoelectric information from each thermoelectric junction and processing the thermoelectric information received from all of the thermoelectric junctions to provide a set of composite characteristics for identifying the given unknown material based upon the set of composite characteristics derived from the thermoelectric information received from all of the thermoelectric junctions.

15. The invention of claim 14 wherein the selected known characteristic is material composition and each test element is constructed of a material having a composition different from the other test elements such that the thermoelectric information provided by each thermoelectric junction is in the form of a thermoelectric voltage related to the material composition of the test element of the corresponding thermoelectric junction.

16. The invention of claim 14 or 15 wherein the test elements are presented to the given unknown material such that all of the test elements are in contact with the unknown material when the thermoelectric information is received from each thermoelectric junction.

17. The invention of claim 16 including substantially equalizing the pressures with which the test elements contact the unknown material at the thermoelectric junctions.

18. The invention of claim 17 including heating the test elements to heat the thermoelectric junctions.

19. The invention of claim 18 wherein the thermoelectric junctions are heated to a controlled, relatively stable known temperature.

* * * * *

UNITED STATES PATENT AND TRADEMARK OFFICE
CERTIFICATE OF CORRECTION

PATENT NO. : 4,542,345
DATED : September 17, 1985
INVENTOR(S) : Walter Tomasulo

It is certified that error appears in the above—identified patent and that said Letters Patent is hereby corrected as shown below:

Column 6, line 11, "moelectric" should read

-- moelectric junctions; and --

Column 7, line 7, "methdd" should read -- method --

Signed and Sealed this

Seventh Day of February, 1989

*Attest:*

DONALD J. QUIGG

*Attesting Officer*     *Commissioner of Patents and Trademarks*